(12) United States Patent
Kruck et al.

(10) Patent No.: US 11,786,452 B2
(45) Date of Patent: Oct. 17, 2023

(54) METHOD FOR DYEING KERATINOUS MATERIAL

(71) Applicant: Henkel AG & Co. KGaA, Duesseldorf (DE)

(72) Inventors: Constanze Kruck, Grevenbroich (DE); Sandra Hilbig, Bochum (DE); Daniela Kessler-Becker, Leverkusen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/620,091

(22) PCT Filed: Apr. 20, 2020

(86) PCT No.: PCT/EP2020/060970
§ 371 (c)(1),
(2) Date: Dec. 16, 2021

(87) PCT Pub. No.: WO2020/254009
PCT Pub. Date: Dec. 24, 2020

(65) Prior Publication Data
US 2022/0370330 A1  Nov. 24, 2022

(30) Foreign Application Priority Data
Jun. 19, 2019 (DE) .................. 10 2019 208 901.1

(51) Int. Cl.
*A61Q 5/10* (2006.01)
*A61K 8/89* (2006.01)
*A61K 8/34* (2006.01)

(52) U.S. Cl.
CPC ............... *A61K 8/89* (2013.01); *A61K 8/342* (2013.01); *A61Q 5/10* (2013.01); *A61K 2800/438* (2013.01); *A61K 2800/4322* (2013.01); *A61K 2800/5424* (2013.01); *A61K 2800/5426* (2013.01)

(58) Field of Classification Search
CPC .. A61K 8/89; A61K 8/342; A61K 2800/4322; A61K 2800/438; A61K 2800/5424; A61K 2800/5426; A61K 8/19; A61K 8/26; A61K 8/29; A61K 8/345; A61K 8/898; A61Q 5/10; A61Q 5/065
USPC ............................................................. 8/405
See application file for complete search history.

(56) References Cited

FOREIGN PATENT DOCUMENTS

| DE | 102018222022 A1 * | 6/2020 | ............ A61Q 5/10 |
|---|---|---|---|
| EP | 3058987 A1 | 8/2016 | |
| FR | 3045346 A1 | 6/2017 | |
| WO | 2012021577 A1 | 2/2012 | |
| WO | WO 2017/108828 A1 * | 6/2017 | ............ A61Q 5/065 |
| WO | 2018115792 A1 | 6/2018 | |
| WO | 2018206457 A1 | 11/2018 | |

\* cited by examiner

*Primary Examiner* — Eisa B Elhilo
(74) *Attorney, Agent, or Firm* — Lorenz & Kopf, LLP

(57) ABSTRACT

A process for dyeing keratinous material is provided. The process includes (1) applying a coloring agent (a) to the keratinous material. The coloring agent (a) includes (a1) at least one amino-functionalized silicone polymer and (a2) at least one colorant compound. The method further includes (2) allowing the coloring agent (a) to act on the keratinous material for a period of 15 seconds to 10 minutes, and (3) rinsing out the dye (a) under running water for a period of 15 seconds to 10 minutes. In the process, no further cosmetic agent other than the coloring agent (a) is used.

19 Claims, No Drawings

METHOD FOR DYEING KERATINOUS MATERIAL

CROSS-REFERENCE TO RELATED APPLICATION

This application is a U.S. National-Stage entry under 35 U.S.C. § 371 based on International Application No. PCT/EP2020/060970, filed Apr. 20, 2020, which was published under PCT Article 21(2) and which claims priority to German Application No. 10 2019 208 901.1, filed Jun. 19, 2019, which are all hereby incorporated in their entirety by reference.

TECHNICAL FIELD

The subject of the present application is a process for dyeing keratinous material, in particular human hair, which comprises the application of a dyeing agent (a), the dyeing agent comprising at least one amino-functionalized silicone polymer and at least one colorant compound. Characteristic of the process is a contact time of the agent on the keratin material of 15 seconds to 10 minutes and the subsequent rinsing of the colorant under running water for a period of 15 seconds to 10 minutes.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeing's with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between 5 and 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeing's, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes.

BRIEF SUMMARY

A process for dyeing keratinous material is provided. The process includes (1) applying a coloring agent (a) to the keratinous material. The coloring agent (a) includes (a1) at least one amino-functionalized silicone polymer and (a2) at least one colorant compound. The method further includes (2) allowing the coloring agent (a) to act on the keratinous material for a period of 15 seconds to 10 minutes, and (3) rinsing out the dye (a) under running water for a period of 15 seconds to 10 minutes. In the process, no further cosmetic agent other than the coloring agent (a) is used.

DETAILED DESCRIPTION following detailed description is merely exemplary in nature and is not intended to limit the disclosure or the application and uses of the subject matter as described herein. Furthermore, there is no intention to be bound by any theory presented in the preceding background or the following detailed description.

It was the object of the present disclosure to provide a dyeing process having fastness properties comparable to oxidative dyeing. Wash fastness properties should be outstanding, but the use of oxidation dye precursors normally used for this purpose should be avoided. A technology was sought that would make it possible to fix the colorant compounds (especially pigments) known from the prior art to the hair in an extremely durable manner. When the agents are used in a dyeing process, intensive dyeing results with good fastness properties should be obtained. In particular, the application of the corresponding processes should result in particularly washfast colorations that do not suffer any weakening of the color intensity even after repeated combing or styling. Compared to the processes already known from the prior art, staining should be made possible with simplified application and increased user comfort.

Surprisingly, it has now been found that the task can be excellently solved if keratinous materials, in particular hair, are dyed by a process in which a dyeing agent (a) is applied to the keratinous materials (hair), allowed to act and then rinsed out again under running water. Here, the colorant (a) comprises at least one amino-functionalized silicone polymer (a1) and at least one color-imparting compound (a2).

During application, the amino silicones (a1) contained in the agent form a film of the keratin material into which the coloring compound (a2) is incorporated.

Surprisingly, it was observed that the color-imparting compounds (a2), when used simultaneously with the amino silicone (a1), attached to the latter or formed a common layer with it. This joint layer formation of (a1) and (a2) means that colorations with high color intensity can be obtained, even without the need for diffusion of the colorant compound into the hair fiber.

Furthermore, it was found that when amino silicone (a1) and colorant compound (a2) were deposited together, very stable layers could be formed, especially when optimum pH values were selected during the application process. Particularly resistant layers could be obtained if (a1) and (a2) were first applied to the keratin materials in a neutral to basic environment and the pH was subsequently lowered. The work leading to this present disclosure has shown that the lowering of the pH could be achieved particularly effectively and uniformly by rinsing the agent under running water. For this purpose, it was not necessary to use other additional agents different from colorant (a) in the process as contemplated herein.

A first object of the present disclosure is a method for coloring keratinous material, in particular human hair, comprising the following steps:

(1) Application of a coloring agent (a) to the keratinous material, wherein the coloring agent (a) comprises:
(a1) at least one amino-functionalized silicone polymer, and
(a2) at least one colorant compound,
(2) Allowing the colorant (a) to act on the keratinous material for a period of 15 seconds to 10 minutes, and
(3) Rinse out the dye (a) under running water for a period of 15 seconds to 10 minutes, exemplified in that no further cosmetic agent other than the coloring agent (a) is used in the process.

Keratinic Material

Keratinous material includes hair, skin, nails (such as fingernails and/or toenails). Wool, furs and feathers also fall under the definition of keratinous material. Preferably, keratinous material is understood to be human hair, human skin and human nails, especially fingernails and toenails. Keratinous material is understood to be human hair.

Dyeing Agent (a)

In step (1) of the process as contemplated herein, the colorant (a) is applied to the keratinous material, to keratinous fibers.

The colorant (a) is exemplified by its content of the constituents (a1) and (a2) essential to the present disclosure.

Amino Functionalized Silicone Polymer (a1) in Colorant (a)

As the first ingredient (a1) essential to the present disclosure, the colorant (a) comprises at least one amino-functionalized silicone polymer. The amino-functionalized silicone polymer may alternatively be referred to as amino silicone or amodimethicone.

Silicone polymers are generally macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than 107 g/mol, preferably not more than 106 g/mol, and particularly preferably not more than 105 g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized polydimethylsiloxane which carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, good effects could be obtained with amino-functionalized silicone polymers (a1) if they carry at least one primary, at least one secondary and/or at least one tertiary amino group. However, dyeing's with the best wash fastness were observed when an amino-functionalized silicone polymer (a1) containing at least one secondary amino group was used in colorant (a).

In a very particularly preferred embodiment, a process as contemplated herein is exemplified in that the colorant (a) comprises at least one amino-functionalized silicone polymer (a1) having at least one secondary amino group.

The secondary amino group(s) may be located at various positions on the amino-functionalized silicone polymer. Particularly good effects were found when an amino-functionalized silicone polymer (a1) was used that has at least one, preferably several, structural units of the formula (Si amino).

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, a process as contemplated herein is exemplified in that the colorant (a) comprises at least one amino-functionalized silicone polymer (a1) which comprises at least one structural unit of the formula (Si amino),

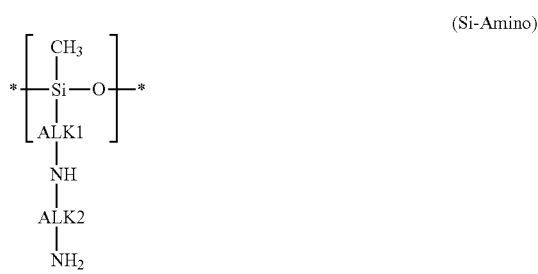
(Si-Amino)

where

ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A divalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—CH($CH_3$)—) and (—$CH_2$—CH($CH_3$)—$CH_2$—).

In another particularly preferred embodiment, the structural units of the formula (Si amino) represent repeat units in the amino-functionalized silicone polymer (a1), so that the silicone polymer comprises multiple structural units of the formula (Si amino).

Particularly well-suited amino-functionalized silicone polymers (a1) with at least one secondary amino group are listed below.

Dyeing's with the very best wash fastnesses could be obtained if, in the process as contemplated herein, at least one colorant (a) containing at least one amino-functionalized silicone polymer (a1) comprising structural units of the formula (Si—I) and of the formula (Si-II) was applied to the keratinous material

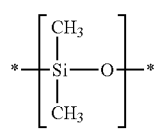
(Si-I)

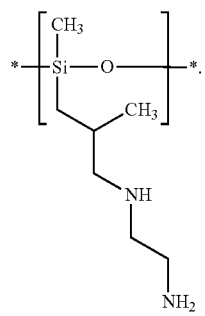
(Si-II)

In a further explicitly quite particularly preferred embodiment, a process as contemplated herein is exemplified in that the colorant (a) comprises at least one amino-functionalized silicone polymer (a1) which comprises structural units of the formula (Si—I) and of the formula (Si-II)

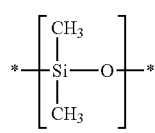
(Si-I)

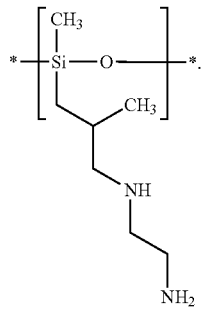
(Si-II)

A corresponding amino functionalized silicone polymer with the structural units (Si—I) and (Si-II) is, for example, the commercial product DC 2-8566 or Dowsil 2-8566 Amino Fluid, which is commercially distributed by the Dow Chemical Company and bears the designation "Siloxanes and Silicones, 3-[(2-aminoethyl)amino]-2-methylpropyl Me, Di-Me-Siloxane" and the CAS number 106842-44-8.

In the context of a further preferred embodiment, a process as contemplated herein is exemplified by the application of an agent (a) to the keratinous material, the coloring agent (a) comprising at least one amino-functional silicone polymer (a1) of the formula of the formula (Si—III),

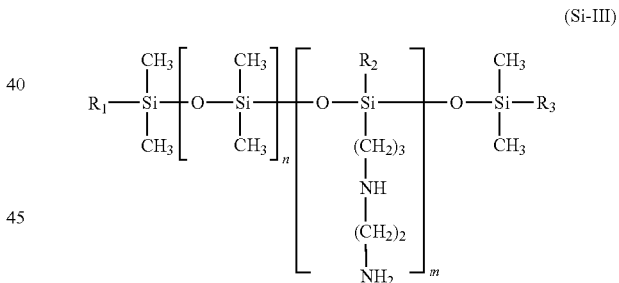
(Si-III)

where
- m and n mean numbers chosen so that the sum (n+m) is in the range 1 to 1000,
- n is a number in the range 0 to 999 and m is a number in the range 1 to 1000,
- R1, R2 and R3, which are the same or different, denote a hydroxy group or a $C_1$-4 alkoxy group,
- wherein at least one of R1 to R3 represents a hydroxy group;

Further methods preferred as contemplated herein are exemplified by the application of an agent (a) to the keratinous material, the colorant (a) comprising at least amino-functional silicone polymer (a1) of the formula of formula (Si-IV), (Si-IV)

$$R_1-\underset{\underset{CH_3}{|}}{\overset{\overset{CH_3}{|}}{Si}}-\left[O-\underset{\underset{CH_3}{|}}{\overset{\overset{CH_3}{|}}{Si}}\right]_p-\left[O-\underset{\underset{\underset{\underset{\underset{NH_2}{|}}{(CH_2)_2}}{|}}{\underset{(CH_2)_3}{|}}}{\overset{\overset{CH_3}{|}}{Si}}\right]_q-O-\underset{\underset{CH_3}{|}}{\overset{\overset{CH_3}{|}}{Si}}-R_2$$

located in the
- p and q mean numbers chosen so that the sum (p+q) is in the range 1 to 1000,
- p is a number in the range 0 to 999 and q is a number in the range 1 to 1000,
- R1 and R2, which are different, denote a hydroxy group or a C1-4 alkoxy group, at least one of R1 to R2 denoting a hydroxy group.

The silicones of the formulas (Si—III) and (Si-IV) differ in the grouping at the Si atom, which carries the nitrogen-containing group: In formula (Si—III), R2 represents a hydroxy group or a C1-4 alkoxy group, while the residue in formula (Si-IV) is a methyl group. The individual Si groupings, which are marked with the indices m and n or p and q, do not have to be present as blocks; rather, the individual units can also be present in a statistically distributed manner, i.e., in the formulas (Si—III) and (Si-IV), not every R1-Si(CH$_3$)$_2$ group is necessarily bonded to an [O—Si(CH$_3$)$_2$] grouping.

Processes as contemplated herein in which a colorant (a) containing at least one amino-functional silicone polymer (a1) of the formula of the formula (Si-V) is applied to the keratin fibers have also proved to be particularly effective with respect to the desired effects (Si-V)

located in the
- A represents a group —OH, —O—Si(CH$_3$)$_3$, —O—Si(CH$_3$)$_2$OH, —O—Si(CH$_3$)$_2$OCH$_3$,
- D represents a group —H, —Si(CH$_3$)$_3$, —Si(CH$_3$)$_2$OH, —Si(CH$_3$)$_2$OCH$_3$,
- b, n and c stand for integers between 0 and 1000,
- with the specifications
  - n>0 and b+c>0
  - at least one of the conditions A=-OH or D=-H is fulfilled.

In the above formula (Si-V), the individual siloxane units are statistically distributed with the indices b, c and n, i.e., they do not necessarily have to be block copolymers.

The colorant (a) may further comprise one or more different amino-functionalized silicone polymers represented by the formula (Si-VI)

$$M(R_aQ_bSiO_{(4-a-b)/2})_x(R_cSiO_{(4-c)/2})_yM \quad (Si\text{-}VI)$$

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical containing at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2.000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-containing radicals, such as mercaptoethyl, mercaptopropyl, mercaptohexyl, mercaptophenyl and the like; preferably R is an alkyl radical containing from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional residue containing at least one amino functional group. One possible formula for Z is NH(CH$_2$)$_z$NH$_2$, where z is 1 or more. Another possible formula for Z is —NH(CH$_2$)$_z$(CH 2)$_{zz}$NH, wherein both z and zz are independently 1 or more, this structure comprising diamino ring structures, such as piperazinyl. Z is most preferably an —NHCH$_2$CH$_2$NH$_2$ residue. Another possible formula for Z is —N(CH$_2$)$_z$(CH$_2$)$_{zz}$NX$_2$ or —NX$_2$, wherein each X of X2 is independently selected from the group including hydrogen and alkyl groups having 1 to 12 carbon atoms, and zz is 0.

Q is most preferably a polar, amine-functional radical of the formula —CH$_2$CH$_2$CH$_2$NHCH$_2$CH$_2$NH$_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$SiO$_{(4-a-b)/2}$ units to R$_c$SiO$_{(4-c)/2}$ units is in the range of about 1:2 to 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, a method as contemplated herein is exemplified by the application of an agent (a) to the keratinous material, wherein the colorant (a) is an amino-functional silicone polymer of the formula (Si-VII)

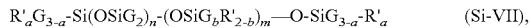   (Si-VII), wherein means:
G is -H, a phenyl group, —OH, —O—$CH_3$, —$CH_3$, —O—$CH_2CH_3$, —$CH_2CH_3$, —O—$CH_2CH_2CH_3$, —$CH_2CH_2CH_3$, —O—$CH(CH_3)_2$, —$CH(CH_3)_2$, —O—$CH_2CH_2CH_2CH_3$, —$CH_2CH_2CH_2CH_3$, —O—$CH_2CH(CH_3)_2$, —$CH_2CH(CH_3)_2$, —O—CH($CH_3$)$CH_2CH_3$, —CH($CH_3$)$CH_2CH_3$, —O—C($CH_3$)$_3$, —C($CH_3$)$_3$;
a stands for a number between 0 and 3, especially 0;
b stands for a number between 0 and 1, especially 1,
m and n are numbers whose sum (m+n) is between 1 and 2000, preferably between 50 and 150, where n preferably assumes values from 0 to 1999 and from 49 to 149 and m preferably assumes values from 1 to 2000, from 1 to 10,
R' is a monovalent radical selected from
-Q-N(R")—$CH_2$—$CH_2$—N(R")$_2$
-Q-N(R")$_2$
-Q-N$^+$(R")$_3$A$^-$
-Q-N$^+$H(R")$_2$A$^-$
-Q-N+H$_2$(R")A$^-$
-Q-N(R")—$CH_2$—$CH_2$—N$^+$R"H$_2$A$^-$,
where each Q is a chemical bond, —$CH_2$—, —$CH_2$—$CH_2$—, —$CH_2CH_2CH_2$—, —C($CH_3$)$_2$—, —$CH_2CH_2CH_2CH_2$—, —$CH_2C(CH_3)_2$—, —CH($CH_3$)$CH_2CH_2$—, R" represents identical or different radicals selected from the group including —H, -phenyl, -benzyl, —$CH_2$—CH($CH_3$)Ph, the $C_{1-20}$ alkyl radicals, preferably —$CH_3$, —$CH_2CH_3$, —$CH_2CH_2CH_3$, —CH($CH_3$)$_2$, —$CH_2CH_2CH_2H3$, —$CH_2CH(CH_3)_2$, —CH($CH_3$)$CH_2CH_3$, —C($CH_3$)$_3$, and A represents an anion preferably selected from chloride, bromide, iodide or methosulfate.

In the context of a further preferred embodiment, a process as contemplated herein is exemplified by the application of an agent (a) to the keratinous material, the coloring agent (a) comprising at least one amino-functional silicone polymer (a1) of the formula (Si-VIIa),

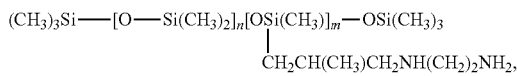   (Si-VIIa)

wherein m and n are numbers whose sum (m+n) is between 1 and 2000, preferably between 50 and 150, n preferably assuming values from 0 to 1999 and from 49 to 149, and m preferably assuming values from 1 to 2000, from 1 to 10.

According to the INCI declaration, these silicones are called trimethylsilylamodimethicones.

In a further preferred embodiment, a process as contemplated herein is exemplified by the application of an agent (a) to the keratinous material, the colorant (a) comprising at least one amino-functional silicone polymer of the formula (Si-VIIb)

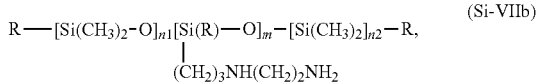   (Si-VIIb)

in which R represents —OH, —O—$CH_3$ or a —$CH_3$ group and m, n1 and n2 are numbers whose sum (m+n1+n2) is between 1 and 2000, preferably between 50 and 150, the sum (n1+n2) preferably assuming values from 0 to 1999 and from 49 to 149 and m preferably assuming values from 1 to 2000, from 1 to 10.

According to the INCI declaration, these amino-functionalized silicone polymers are called amodimethicones.

Regardless of which amino-functional silicones are used, colorants (a) as contemplated herein are preferred which contain an amino-functional silicone polymer whose amine number is above 0.25 meq/g, preferably above 0.3 meq/g and above 0.4 meq/g. The amine number represents the milliequivalents of amine per gram of the amino-functional silicone. The amine number represents the milliequivalents of amine per gram of the amino-functional silicone.

Furthermore, colorants (a) which contained a special 4-morpholinomethyl-substituted silicone polymer (a1) are also suitable for use in the process as contemplated herein. This amino-functionalized silicone polymer comprises structural units of the formulae (SI-VIII) and of the formula (Si-IX)

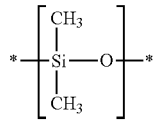   (Si-VIII)

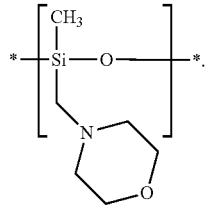   (Si-IX)

Corresponding 4-morpholinomethyl-substituted silicone polymers are described below.

A very particularly preferred amino-functionalized silicone polymer is known by the name of Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X)

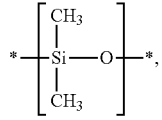   (Si-VIII),

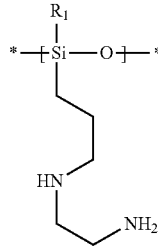   (Si-X)

-continued

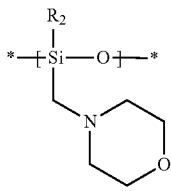
(Si-IX)

in which
R1 is —CH₃, —OH, —OCH₃, —O—CH₂CH₃, —O—CH₂CH₂CH₃, or —O—CH(CH₃)₂;
R2 is —CH₃, —OH, or —OCH₃.

Particularly preferred colorants (a) as contemplated herein contain at least one 4-morpholinomethyl-substituted silicone of the formula (Si-XI)

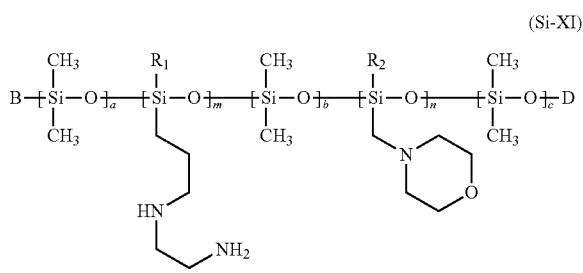
(Si-XI)

located in the
R1 is —CH₃, —OH, —OCH₃, —O—CH₂CH₃, —O—CH₂CH₂CH₃, or —O—CH(CH₃)₂;
R2 is —CH₃, —OH, or —OCH₃.
B represents a group —OH, —O—Si(CH₃)₃, —O—Si(CH₃)₂OH, —O—Si(CH₃)₂OCH₃,
D represents a group —H, —Si(CH₃)₃, —Si(CH₃)₂OH, —Si(CH₃)₂OCH₃,
a, b and c stand independently for integers between 0 and 1000, with the condition a+b+c>0
m and n independently of each other stand for integers between 1 and 1000 with the proviso that
at least one of the conditions B=-OH or D=-H is fulfilled,
the units a, b, c, m and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m and n are preferably statistically distributed.

The silicones used as contemplated herein represented by formula (Si-VI) can be trimethylsilyl-terminated (D or B=-Si(CH₃)₃), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which
B=—O—Si(CH₃)₂OH and D=-Si(CH₃)₃
B=—O—Si(CH₃)₂OH and D=-Si(CH₃)₂OH
B=—O—Si(CH₃)₂OH and D=-Si(CH₃)₂OCH₃
B=-O—Si(CH₃)₃ and D=-Si(CH₃)₂OH
B=—O—Si(CH₃)₂OCH₃ and D=-Si(CH₃)₂OH to everyone. These silicones lead to exorbitant improvements in the hair properties of the hair treated with the agents of the present disclosure, and to a seriously improved protection in oxidative treatment.

The colorant (a) used in the process as contemplated herein is a premix or concentrate which contains the amino-functionalized silicone polymers (a1) as a main component.

It has been found to be particularly advantageous if the agent as contemplated herein contains the amino-functionalized silicone polymer(s) (a1) in certain quantity ranges. Particularly good results were obtained when the agent contained—based on the total weight of the agent—a total amount of 0.1 to 8.0% by weight, preferably 0.02 to 5.0% by weight, more preferably 0.1 to 3.0% by weight and very particularly preferably 0.05 to 3.5% by weight.

In another particularly preferred embodiment, a process as contemplated herein is exemplified in that the colorant (a) contains—based on the total weight of the colorant (a)—one or more amino-functionalized silicone polymers (a1) in a total amount of from 0.1 to 8.0% by weight, preferably from 0.02 to 5.0% by weight, more preferably from 0.1 to 3.0% by weight and very particularly preferably from 0.05 to 3.5% by weight.

Colorant Compound (a2) in Colorant (a)

As a second constituent essential to the present disclosure, the colorant (a) used in the process as contemplated herein contains at least one color-imparting compound (a2).

For the purposes of the present disclosure, colorant compounds are substances capable of imparting a coloration to the keratin material. Particularly well-suited colorant compounds can be selected from the group of pigments, direct-acting dyes, photochromic dyes and thermochromic dyes.

In a further preferred embodiment, a process as contemplated herein is exemplified in that the colorant (a) comprises at least one colorant compound (a2) from the group including pigments, direct dyes, photochromic dyes and thermochromic dyes.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, a colorant (a) as contemplated herein is exemplified in that it comprises at least one colorant compound (a2) from the group including inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, a process as contemplated herein is exemplified in that the colorant (a) comprises at least one colorant compound (a2) from the group of inorganic pigments, which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, a composition as contemplated herein is exemplified in that it comprises (a) at least one colorant compound (a2) from the group of pigments selected from mica- or mica-based pigments which are reacted with one or more metal oxides from the group including titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:

Colorona Copper, Merck, MICA, CI 77491 (IRON OXIDES)

Colorona Passion Orange, Merck, Mica, CI 77491 (Iron Oxides), Alumina

Colorona Patina Silver, Merck, MICA, CI 77499 (IRON OXIDES), CI 77891 (TITANIUM DIOXIDE)

Colorona RY, Merck, CI 77891 (TITANIUM DIOXIDE), MICA, CI 75470 (CARMINE)

Colorona Oriental Beige, Merck, MICA, CI 77891 (TITANIUM DIOXIDE), CI 77491 (IRON OXIDES)

Colorona Dark Blue, Merck, MICA, TITANIUM DIOXIDE, FERRIC FERROCYANIDE

Colorona Chameleon, Merck, CI 77491 (IRON OXIDES), MICA

Colorona Aborigine Amber, Merck, MICA, CI 77499 (IRON OXIDES), CI 77891 (TITANIUM DIOXIDE)

Colorona Blackstar Blue, Merck, CI 77499 (IRON OXIDES), MICA

Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891 (TITANIUM DIOXIDE)

Colorona Russet, Merck, CI 77491 (TITANIUM DIOXIDE), MICA, CI 77891 (IRON OXIDES)

Colorona Imperial Red, Merck, MICA, TITANIUM DIOXIDE (CI 77891), D&C RED NO. 30 (CI 73360)

Colorona Majestic Green, Merck, CI 77891 (TITANIUM DIOXIDE), MICA, CI 77288 (CHROMIUM OXIDE GREENS)

Colorona Light Blue, Merck, MICA, TITANIUM DIOXIDE (CI 77891), FERRIC FERROCYANIDE (CI 77510)

Colorona Red Gold, Merck, MICA, CI 77891 (TITANIUM DIOXIDE), CI 77491 (IRON OXIDES)

Colorona Gold Plus MP 25, Merck, MICA, TITANIUM DIOXIDE (CI 77891), IRON OXIDES (CI 77491)

Colorona Carmine Red, Merck, MICA, TITANIUM DIOXIDE, CARMINE

Colorona Blackstar Green, Merck, MICA, CI 77499 (IRON OXIDES)

Colorona Bordeaux, Merck, MICA, CI 77491 (IRON OXIDES)

Colorona Bronze, Merck, MICA, CI 77491 (IRON OXIDES)

Colorona Bronze Fine, Merck, MICA, CI 77491 (IRON OXIDES)

Colorona Fine Gold MP 20, Merck, MICA, CI 77891 (TITANIUM DIOXIDE), CI 77491 (IRON OXIDES)

Colorona Sienna Fine, Merck, CI 77491 (IRON OXIDES), MICA

Colorona Sienna, Merck, MICA, CI 77491 (IRON OXIDES)

Colorona Precious Gold, Merck, Mica, CI 77891 (Titanium dioxide), Silica, CI 77491(Iron oxides), Tin oxide Colorona Sun Gold Sparkle MP 29, Merck, MICA, TITANIUM DIOXIDE, IRON OXIDES, MICA, CI 77891, CI 77491 (EU)

Colorona Mica Black, Merck, CI 77499 (Iron oxides), Mica, CI 77891 (Titanium dioxide)

Colorona Bright Gold, Merck, Mica, CI 77891 (Titanium dioxide), CI 77491(Iron oxides)

Colorona Blackstar Gold, Merck, MICA, CI 77499 (IRON OXIDES)

Other particularly preferred color pigments with the trade name Xirona® are for example:

Xirona Golden Sky, Merck, Silica, CI 77891 (Titanium Dioxide), Tin Oxide

Xirona Caribbean Blue, Merck, Mica, CI 77891 (Titanium Dioxide), Silica, Tin Oxide Xirona Kiwi Rose, Merck, Silica, CI 77891 (Titanium Dioxide), Tin Oxide Xirona Magic Mauve, Merck, Silica, CI 77891 (Titanium Dioxide), Tin Oxide.

In addition, particularly preferred color pigments with the trade name Unipure® are for example:

Unipure Red LC 381 EM, Sensient CI 77491 (Iron Oxides), Silica

Unipure Black LC 989 EM, Sensient, CI 77499 (Iron Oxides), Silica

Unipure Yellow LC 182 EM, Sensient, CI 77492 (Iron Oxides), Silica

In a further embodiment, the composition as contemplated herein may also comprise (a) one or more colorant compounds (a2) from the group including organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyorrole, indigo, thioindido, dioxazine and/or triarylmethane compounds.

Examples of particularly suitable organic pigments are carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In a further particularly preferred embodiment, a process as contemplated herein is exemplified in that the colorant (a) comprises at least one colorant compound (a2) from the group of organic pigments which is preferably selected from the group including carmine, quinacridone, phthalocyanine, sorghum, blue pigments having the Color Index numbers Cl 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the above pigments in the colorant (a) of the process as contemplated herein is particularly preferred. It is also preferred if the pigments used have a certain particle size. As contemplated herein, it is therefore advantageous if the at least one pigment has an average particle size $D_{50}$ of 1.0 to 50 μm, preferably 5.0 to 45 μm, preferably 10 to 40 μm, 14 to 30 μm. The mean particle size $D_{50}$, for example, can be determined using dynamic light scattering (DLS).

The coloring compounds (a2), the coloring compounds from the group of pigments, represent the second essential component of the coloring agent (a) as contemplated herein. The pigment or pigments are also particularly preferred in the appropriate ranges of amounts in the colorant (a). Particularly good results were obtained when the colorant (a)-based on the total weight of the agent (a)-contained one or more pigments in a total amount of from 0.01 to 10.0% by weight, preferably from 0.1 to 5.0% by weight, more preferably from 0.2 to 2.5% by weight and very particularly preferably from 0.25 to 1.5% by weight.

In another very particularly preferred embodiment, a process as contemplated herein is exemplified in that the colorant (a) contains—based on the total weight of the colorant (a)—one or more pigments (a2) in a total amount of from 0.01 to 10.0% by weight, preferably from 0.1 to 5.0% by weight, more preferably from 0.2 to 2.5% by weight and very particularly preferably from 0.25 to 1.5% by weight.

As colorant compounds (a2), the colorants (a) used in the process as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments. Preferably, the direct dyes within the meaning of the present disclosure have a solubility in water (760 mmHg) at 25° C. of more than 1.0 g/L.

Direct dyes can be divided into anionic, cationic and non-ionic direct dyes.

In a further embodiment, a process as contemplated herein is exemplified in that the colorant (a) comprises at least one colorant compound (a2) from the group including anionic, nonionic and cationic direct dyes.

Suitable cationic direct dyes include Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethy)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

In the course of the work leading to the present disclosure, it has been found that dyeing's with good color intensities and fastness properties can also be produced with agents (a) containing at least one anionic direct dye (a2).

In a further embodiment, a process as contemplated herein is therefore exemplified in that the colorant (a) comprises at least one anionic direct dye.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO$^-$, —SO$_3^-$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In another embodiment, a process for dyeing keratinous material is exemplified in that the dyeing composition (a) comprises at least one anionic direct dye selected from the group including nitrophenylenediamines, nitroaminophenols, azo dyes, anthraquinone dyes, triarylmethane dyes, xanthene dyes, rhodamine dyes, oxazine dyes and/or indophenol dyes, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

Suitable acid dyes may include, for example, one or more compounds selected from the following group: Acid Yellow 1 (D&C Yellow 7, Citronin A, Ext. D&C Yellow No. 7, Japan Yellow 403,CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C.015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1;CI 20170;KATSU201;nosodiumsalt;Brown No. 201;RESORCIN BROWN;ACID ORANGE 24;Japan Brown 201;D & C Brown No. 1), Acid Red 14 (C.I.14720), Acid Red 18 (E124, Red 18; CI 16255), Acid Red 27 (E 123, CI 16185, C-Rot 46, Real red D, FD&C Red Nr.2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C.53, CI 45410), Acid Red 95 (CI 45425, Erythtosine,Simacid Erythrosine Y), Acid Red 184 (CI 15685), Acid Red 195, Acid Violet 43 (Jarocol Violet 43, Ext. D&C Violet n° 2, C.I. 60730, COLIPA n° C.063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has a very high water solubility of more than 20% by weight.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl} {4-[(N-ethyl(3-sulfonatobenzyl)imino]-2,5-cyclohexadien-1-ylidene}methyl)-benzenesulfonate and has a solubility in water of more than 20% by weight (25° C.).

In a further embodiment, a process as contemplated herein is therefore exemplified in that the colorant (a) comprises at least one direct dye (a2) selected from the group including acid yellow 1, acid yellow 3, acid yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dye(s) can be used in different amounts in the colorant (a) depending on the desired color intensity. Particularly good results could be obtained if the colorant (a)—based on the total weight of the agent (a)—contains one or more direct dyes (b) in a total amount of from 0.01 to 10.0% by weight, preferably from 0.1 to 8.0% by weight, more preferably from 0.2 to 6.0% by weight and most preferably from 0.5 to 4.5% by weight.

Furthermore, the colorant (a) may also contain at least one photochromic or thermochromic dye as the coloring compound (a2).

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (Thermochromism).

The coloring agent (a) may contain—based on the total weight of the agent (a)—one or more photochromic dyes (b) in a total amount of from 0.01 to 10.0% by weight, preferably from 0.1 to 8.0% by weight, more preferably from 0.2 to 6.0% by weight, and most preferably from 0.5 to 4.5% by weight The coloring agent (a) may contain—based on the total weight of the agent (a)—one or more thermochromic dyes (b) in a total amount of from 0.01 to 10.0% by weight, preferably from 0.1 to 8.0% by weight, more preferably from 0.2 to 6.0% by weight, and most preferably from 0.5 to 4.5% by weight Solvent (a3) in the Colorant (a)

The use of solvents (a3) continued to produce very good results. For this reason, the colorant (a) as contemplated herein may therefore additionally contain at least one solvent as an optional component (a3).

Suitable solvents (a3) may include, for example, solvents selected from the group including 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol. The use of 1,2-propylene glycol is particularly preferred.

In another particularly preferred embodiment, a process as contemplated herein is exemplified in that the colorant (a) comprises at least one solvent (a3) selected from the group including 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol, very preferably 1,2-propylene glycol.

1,2-Propylene glycol is alternatively referred to as 1,2-propanediol and has CAS numbers 57-55-6 [(RS)-1,2-dihydroxypropane], 4254-14-2 [(R)-1,2-dihydroxypropane], and 4254-15-3 [(S)-1,2-dihydroxypropane]. Ethylene glycol is alternatively known as 1,2-ethanediol and carries CAS number 107-21-1. Glycerol is alternatively known as 1,2,3-propanetriol and carries CAS number 56-81-5. Phenoxyethanol has the Cas number 122-99-6.

All the solvents described previously are commercially available from various chemical suppliers, such as Aldrich or Fluka.

By using the above-mentioned solvents in suitable amounts, a particularly stable colorant (a) can be obtained which can be mixed with the agent (b) particularly quickly and uniformly. Also, when the suitable and preferred solvents (a3) were used, when 1,2-propylene glycol was used, color results with very high intensity were obtained on keratin fibers.

In a further preferred embodiment, a process as contemplated herein is exemplified in that the colorant (a) contains—based on the total weight of the agent (a)—one or more solvents (a3) in a total amount of 0.25 to 20.0% by weight, preferably 2.0 to 15.0% by weight, more preferably 3.0 to 15.0% by weight and very particularly preferably 4.0 to 10.0% by weight of 1,2-propylene glycol.

In another very particularly preferred embodiment, a process as contemplated herein is exemplified in that the colorant (a) contains—based on the total weight of the agent (a)—0.25 to 95.0% by weight, preferably 2.0 to 15.0% by weight, more preferably 3.0 to 15.0% by weight and very particularly preferably 4.0 to 10.0% by weight of 1,2-propylene glycol (a3).

Fat Components (a4)

As a further optional constituent, the composition as contemplated herein particularly preferably contains at least one fat constituent (a4). It has been found that the use of at least one fatty ingredient (a4) results in the agent being in the form of an emulsion, which has the optimum viscosity and has also been found to be beneficial in terms of improving color intensity.

The fatty components are hydrophobic substances that can form emulsions in the presence of water, forming micelle systems. Without being committed to this theory, it is assumed that the $C_1$-$C_6$ alkoxysilanes—either in the form of their monomers or possibly in the form of their condensed oligomers—are embedded in this hydrophobic environment or in the micelle systems so that the polarity of their environment changes. Due to the hydrophobic character of the fatty components, the environment of the $C_1$-$C_6$ alkoxysilanes is also hydrophobized. It is assumed that the polymerization reaction of the $C_1$-$C_6$ alkoxy silanes leading to the film or coating takes place in an environment of reduced polarity at reduced speed.

For the purposes of the present disclosure, "fatty components" means organic compounds with a solubility in water at room temperature (22° C.) and atmospheric pressure (760 mmHg) of less than 1% by weight, preferably less than 0.1% by weight. The definition of fat constituents explicitly covers only uncharged (i.e., non-ionic) compounds. Fat components have at least one saturated or unsaturated alkyl group with at least 12 C atoms. The molecular weight of the fat constituents is a maximum of 5000 g/mol, preferably a maximum of 2500 g/mol and particularly preferably a maximum of 1000 g/mol. The fat components are neither polyoxyalkylated nor polyglycerylated compounds.

Very preferably, the fat constituents (a4) contained in the composition are selected from the group including $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In the context of a further preferred embodiment, an agent as contemplated herein is exemplified in that it contains one or more fat constituents (a4) from the group including the $C_{12}$-$C_{30}$ fatty alcohols, the $C_{12}$-$C_{30}$ fatty acid triglycerides, the $C_{12}$-$C_{30}$ fatty acid monoglycerides, the $C_{12}$-$C_{30}$ fatty acid diglycerides and/or the hydrocarbons.

In this context, very particularly preferred fat constituents are understood to be constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. For the purposes of the present disclosure, only non-ionic substances are explicitly regarded as fat components. Charged compounds such as fatty acids and their salts are not considered to be fat components.

The $C_{12}$-$C_{30}$ fatty alcohols can be saturated, mono- or polyunsaturated, linear or branched fatty alcohols with 12 to 30 C atoms.

Examples of preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

In another preferred embodiment, an agent as contemplated herein is exemplified in that it comprises one or more $C_{12}$-$C_{30}$ fatty alcohols selected from the group including.
  Dodecan-1-ol (dodecyl alcohol, lauryl alcohol),
  Tetradecan-1-ol (tetradecyl alcohol, myristyl alcohol),
  Hexadecan-1-ol (hexadecyl alcohol, cetyl alcohol, palmityl alcohol), Octadecan-1-ol (octadecyl alcohol, stearyl alcohol),
  Arachyl alcohol (eicosan-1-ol),
  Heneicosyl alcohol (heneicosan-1-ol),
  Behenyl alcohol (docosan-1-ol),
  (9Z)-Octadec-9-en-1-ol (oleyl alcohol),
  (9E)-Octadec-9-en-1-ol (elaidyl alcohol),
  (9Z,12Z)-Octadeca-9,12-dien-1-ol (linoleyl alcohol),
  (9Z,12Z,15Z)-Octadeca-9,12,15-trien-1-ol (linolenoyl alcohol),
  Gadoleyl alcohol ((9Z)-Eicos-9-en-1-ol),
  Arachidonic alcohol ((5Z,8Z,11Z,14Z)-Eicosa-5,8,11,14-tetraen-1-ol),
  Erucyl alcohol ((13Z)-docos-13-en-1-ol),
  Brassidyl alcohol ((13E)-docosen-1-ol),
  2-Octyl-dodecanol,
  2-hexyl dodecanol and/or
  2-Butyl-dodecanol contains.

It has been found to be quite preferable to use one or more $C_{12}$-$C_{30}$ fatty alcohols in quite specific ranges of amounts.

It is particularly preferred if the composition contains one or more $C_{12}$-$C_{30}$ fatty alcohols in a total amount of from 2.0 to 50.0% by weight, preferably from 3.0 to 30.0% by weight, more preferably from 4.0 to 20.0% by weight, still more preferably from 5.0 to 15.0% by weight and most preferably from 5.0 to 10.0% by weight, based on the total weight of the composition.

Further, as a wholly suitable fat ingredient, the composition (a4) may also contain at least one $C_{12}$-$C_{30}$ fatty acid triglyceride that is $C_{12}$-$C_{30}$ fatty acid monoglyceride and/or $C_{12}$-$C_{30}$ fatty acid diglyceride. For the purposes of the present disclosure, a $C_{12}$-$C_{30}$ fatty acid triglyceride is understood to be the triester of the trivalent alcohol glycerol with three equivalents of fatty acid. Both structurally identical and different fatty acids within a triglyceride molecule can be involved in the formation of esters.

As contemplated herein, fatty acids are to be understood as saturated or unsaturated, unbranched or branched, unsubstituted or substituted $C_{12}$-$C_{30}$ carboxylic acids. Unsaturated fatty acids can be mono- or polyunsaturated. For an unsaturated fatty acid, its C=C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, moringa oil, apricot kernel oil, marula oil and/or optionally hardened castor oil are particularly suitable for use in the product as contemplated herein.

A $C_{12}$-$C_{30}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{30}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9, 12-dienoic acid, linolenic acid [(9Z, 12Z,15Z)-octadeca-9, 12,15-trienoic acid, elaeostearic acid [(9Z,11E,13E)- octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{30}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Particularly good results were obtained when composition (B) contained at least one $C_{12}$-$C_{30}$ fatty acid monoglyceride selected from the monoesters of glycerol with one equivalent of fatty acid selected from the group including dodecanoic acid (lauric acid), Tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

In the context of a further embodiment, a composition as contemplated herein is exemplified in that it comprises at least one $C_{12}$-$C_{30}$ fatty acid monoglyceride selected from the monoesters of glycerol with one equivalent of fatty acid from the group including dodecanoic acid, tetradecanoic acid, hexadecanoic acid, tetracosanoic acid, octadecanoic acid, eicosanoic acid and/or docosanoic acid.

It has been shown to be preferable to use one or more $C_{12}$-$C_{30}$ fatty acid mono-, $C_{12}$-$C_{30}$ fatty acid di- and/or $C_{12}$-$C_{30}$ fatty acid triglycerides (a4) in very specific ranges of amounts in the composition.

Regarding the solution of the task as contemplated herein, it has proved advantageous if the agent—based on the total weight of the agent—contained one or more $C_{12}$-$C_{30}$ fatty acid mono-, $C_{12}$-$C_{30}$ fatty acid di- and/or $C_{12}$-$C_{30}$ fatty acid triglycerides in a total amount of 0.1 to 20.0 wt. %, preferably from 0.3 to 15.0% by weight, more preferably from 0.5 to 10.0% by weight, and most preferably from 0.8 to 5.0% by weight.

In a very particularly preferred embodiment, a process as contemplated herein is exemplified in that the composition contains—based on the total weight of the composition—one or more $C_{12}$-$C_{30}$ fatty acid mono-, $C_{12}$-$C_{30}$ fatty acid di- and/or $C_{12}$-$C_{30}$ fatty acid triglycerides in a total amount of from 0.1 to 20.0% by weight, preferably from 0.3 to 15.0% by weight, more preferably from 0.5 to 10.0% by weight and very particularly preferably from 0.8 to 5.0% by weight.

The $C_{12}$-$C_{30}$ fatty acid mono-, $C_{12}$-$C_{30}$ fatty acid di- and/or $C_{12}$-$C_{30}$ fatty acid triglycerides may be used as the sole fat components in the compositions. However, it may also be suitable as contemplated herein to incorporate at least one $C_{12}$-$C_{30}$ fatty acid mono-, $C_{12}$-$C_{30}$ fatty acid di- and/or $C_{12}$-$C_{30}$ fatty acid triglyceride in combination with at least one $C_{12}$-$C_{30}$ fatty alcohol into the composition.

Furthermore, as a very particularly preferred fat constituent, the composition may also contain at least one hydrocarbon.

Hydrocarbons are compounds consisting exclusively of the atoms carbon and hydrogen with 8 to 80 C atoms. In this context, aliphatic hydrocarbons such as mineral oils, liquid paraffin oils (e.g., Paraffinum Liquidum or Paraffinum Perliquidum), isoparaffin oils, semi-solid paraffin oils, paraffin waxes, hard paraffin (Paraffinum Solidum), Vaseline and polydecenes are particularly preferred.

Liquid paraffin oils (Paraffinum Liquidum and Paraffinum Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, consisting mainly of hydrocarbon chains with a C-chain distribution of 25 to 35 C-atoms.

Particularly good results were obtained when the composition contained at least one hydrocarbon selected from the group including mineral oils, liquid kerosene oils, isoparaffin oils, semisolid kerosene oils, kerosene waxes, hard kerosene (Paraffinum solidum), petrolatum and polydecenes.

In a very particularly preferred embodiment, a composition as contemplated herein is exemplified in that it comprises at least one fatty constituent (a4) from the group of hydrocarbons.

Regarding the solution of the problem as contemplated herein, it proved to be quite particularly preferable if the composition contained—based on the total weight of the composition—one or more hydrocarbons in a total amount of from 0.5 to 20.0% by weight, preferably from 0.7 to 10.0% by weight, more preferably from 0.9 to 5.0% by weight and very particularly preferably from 1.0 to 4.0% by weight.

In a very particularly preferred embodiment, an agent as contemplated herein is exemplified in that it contains—based on the total weight of the agent—one or more hydrocarbons (a4) in a total amount of in a total amount of from 0.5 to 20.0% by weight, preferably from 0.7 to 10.0% by weight, more preferably from 0.9 to 5.0% by weight and very particularly preferably from 1.0 to 4.0% by weight.

The hydrocarbon or hydrocarbons may be used as the sole fatty ingredients in the agents. However, it is also as contemplated herein to incorporate at least one hydrocarbon in combination with at least one other constituent into the compositions.

Very preferably, the composition contains at least one fatty constituent from the group of $C_{12}$-$C_{30}$ fatty alcohols and at least one further fatty constituent from the group of hydrocarbons.

Surfactants in the Medium

The agent as contemplated herein is particularly preferably in the form of an emulsion. To further optimize the formation of the emulsion, it has proven particularly preferable to continue to use at least one surfactant in the agent.

Quite preferably, the colorant (a) therefore additionally contains at least one surfactant.

In another particularly preferred embodiment, a process as contemplated herein is exemplified in that the colorant (a) comprises at least one surfactant.

The term surfactants (T) refer to surface-active substances that can form adsorption layers on surfaces and interfaces or aggregate in bulk phases to form micelle colloids or lyotropic mesophases. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

In a very particularly preferred embodiment, an agent as contemplated herein is exemplified in that it comprises at least one nonionic surfactant.

Non-ionic surfactants contain, for example, a polyol group, a polyalkylene glycol ether group or a combination of polyol and polyglycol ether group as the hydrophilic group. Such links include
- Addition products of 2 to 50 mol ethylene oxide and/or 0 to 5 mol propylene oxide to linear and branched fatty alcohols with 6 to 30 C atoms, the fatty alcohol polyglycol ethers or the fatty alcohol polypropylene glycol ethers or mixed fatty alcohol polyethers,
- Addition products of 2 to 50 mol ethylene oxide and/or 0 to 5 mol propylene oxide to linear and branched fatty acids with 6 to 30 C atoms, the fatty acid polyglycol ethers or the fatty acid polypropylene glycol ethers or mixed fatty acid polyethers,
- Addition products of 2 to 50 mol ethylene oxide and/or 0 to 5 mol propylene oxide to linear and branched alkylphenols having 8 to 15 C atoms in the alkyl group, the alkylphenol polyglycol ethers or the alkylpolypropylene glycol ethers or mixed alkylphenol polyethers,
- with a methyl or $C_2$-$C_6$-alkyl radical end-group capped addition products of 2 to 50 moles of ethylene oxide and/or 0 to 5 moles of propylene oxide to linear and branched fatty alcohols with 8 to 30 C atoms, to fatty acids with 8 to 30 C atoms and to alkylphenols with 8 to 15 C atoms in the alkyl group, such as the grades available under the sales names Dehydol® LS, Dehydol® LT (Cognis),
- $C_{12}$-$C_{30}$ fatty acid mono- and diesters of addition products of 1 to 30 mol ethylene oxide to glycerol,
- Addition products of 5 to 60 mol ethylene oxide to castor oil and hardened castor oil,
- Polyol fatty acid esters, such as the commercial product Hydagen® HSP (Cognis) or Sovermol® grades (Cognis),
- alkoxylated triglycerides,
- alkoxylated fatty acid alkyl esters of the formula (Tnio-1)

$$R^1CO—(OCH_2CHR^2)_w OR^3 \qquad \text{(Tnio-1)}$$

in which $R^1CO$ is a linear or branched, saturated and/or unsaturated acyl radical having 6 to 22 carbon atoms, $R^2$ is hydrogen or methyl, $R^3$ is linear or branched alkyl radicals having 1 to 4 carbon atoms and w is numbers from 1 to 20,
- amine oxides,
- Hydroxy mixed ethers, as described for example in DE-OS 19738866,
- Sorbitan fatty acid esters and addition products of ethylene oxide to sorbitan fatty acid esters such as polysorbates,
- Sugar fatty acid esters and addition products of ethylene oxide to sugar fatty acid ester,
- Addition products of ethylene oxide to fatty acid alkanolamides and fatty amines,
- Sugar tensides of the alkyl and alkenyl oligoglycoside type according to formula (E4-II), $$R^4O\text{-}[G]_p \qquad \text{(Tnio-2)}$$

in which $R^4$ is an alkyl or alkenyl radical containing 4 to 22 carbon atoms, G is a sugar residue containing 5 or 6 carbon atoms and p is several 1 to 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula (Tnio-2) indicates the degree of oligomerization (DP), i.e., the distribution of mono- and oligoglycosides and stands for a number between 1 and 10. While p must always be an integer in the individual molecule and can assume the values p=1 to 6, the value p for a certain alkyl oligoglycoside is an analytically determined arithmetical quantity, which usually represents a fractional number. Preferably alkyl and/or alkenyl oligoglycosides with an average degree of oligomerization p of 1.1 to 3.0 are used. From an application technology point of view, those alkyl and/or alkenyl oligoglycosides are preferred whose degree of oligomerization is less than 1.7 and lies between 1.2 and 1.4. The alkyl or alkenyl radical $R^4$ can be derived from primary alcohols containing 4 to 11, preferably 8 to 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or during the hydrogenation of aldehydes from Roelen's oxo synthesis. Preferred are alkyl oligoglucosides with a chain length of $C_8$-$C_{10}$ (DP=1 to 3), which are obtained as a preliminary step in the distillative separation of technical $C_8$-$C_{18}$ coconut-fatty alcohol and may be contaminated with less than 6% by weight of $C_{12}$ alcohol, and alkyl oligoglucosides based on technical $C_{9/11}$ oxoalcohols (DP=1 to 3). The alkyl or alkenyl radical $R^{15}$ can also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Preferred are alkyl oligoglucosides based on hardened $C_{12/14}$ coconut alcohol with a DP of 1 to 3.

Sugar surfactants of the fatty acid N-alkyl polyhydroxyalkylamide type, a nonionic surfactant of formula (Tnio-3)

$$R^5CO—NR^6—[Z] \qquad \text{(Tnio-3)}$$

in which $R^5CO$ is an aliphatic acyl radical containing 6 to 22 carbon atoms, $R^6$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups. The fatty acid N-alkyl polyhydroxyalkylamides are known substances that can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkyl polyhydroxyalkylamides are preferably derived from reducing sugars with 5 or 6 carbon atoms, especially from glucose. The preferred fatty acid N-alkyl polyhydroxyalkylamides are therefore fatty acid N-alkylglucamides as represented by the formula (Tnio-4):

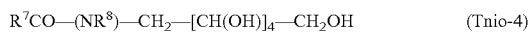

$R^7CO$—$(NR^8)$—$CH_2$—$[CH(OH)]_4$—$CH_2OH$ (Tnio-4)

Preferably, glucamides of the formula (Tnio-4) are used as fatty acid-N-alkyl polyhydroxyalkylamides, in which $R^8$ represents hydrogen or an alkyl group and $R^7C_0$ represents the acyl radical of caproic acid, caprylic acid, capric acid, Lauric acid, myristic acid, palmitic acid, palmoleic acid, stearic acid, isostearic acid, oleic acid, elaidic acid, petroselinic acid, linoleic acid, linolenic acid, arachidic acid, gadoleic acid, behenic acid or erucic acid or their technical mixtures. Particularly preferred are fatty acid N-alkyl glucamides of the formula (Tnio-4), which are obtained by reductive amination of glucose with methylamine and subsequent acylation with lauric acid or C12/14 coconut fatty acid or a corresponding derivative. Furthermore, polyhydroxyalkylamides can also be derived from maltose and palatinose.

The sugar surfactants may preferably be present in the compositions used as contemplated herein in amounts of 0.1-20% by weight, based on the total composition. Amounts of 0.5-15 wt. % are preferred and amounts of 0.5-7.5 wt. % are particularly preferred.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with 2 to 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R contains 6 to 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. By "normal" homologue distribution we mean mixtures of homologues obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Particularly good results were obtained when an agent (b) containing at least one ethoxylated fatty alcohol with a degree of ethoxylation of 80 to 120 was used in the process as contemplated herein.

In another very particularly preferred embodiment, a process as contemplated herein is exemplified in that the colorant (a) comprises at least one nonionic surfactant of the formula (T-I),

$Ra$—$[O$—$CH_2$—$CH_2]_n$—$OH$ (T-I)

wherein Ra represents a saturated or unsaturated, straight or branched $C_8$-$C_{24}$ alkyl group, preferably a saturated, straight $C_{16}$-bis $C_{18}$ alkyl group, and n is an integer from 80 to 120, preferably an integer from 90 to 110, and particularly preferably the number 100.

A particularly well-suited nonionic surfactant of this type bears the trade name Brij S 100 or Brij S 100 PA SG. This is stearyl alcohol, ethoxylated with 100 EO, which is commercially available from Croda and has the CAS number 9005-00-9.

Furthermore, particularly good results were obtained when an agent as contemplated herein was used which contained at least one ethoxylated fatty alcohol with a degree of ethoxylation of 10 to 40.

In another very particularly preferred embodiment, a process as contemplated herein is exemplified in that the colorant (a) comprises at least one nonionic surfactant of the formula (T-I),

$Ra$—$[O$—$CH_2$—$CH_2]_n$—$OH$ (T-I)

wherein
Ra represents a saturated or unsaturated, unbranched or branched $C_8$-$C_{24}$ alkyl group, preferably a saturated, unbranched $C_{16}$- to Cis alkyl group, and
n is an integer from 10 to 40, preferably an integer from 20 to 35, and particularly preferably the number 30.

A particularly well-suited nonionic surfactant of this type is ceteareth-30. Ceteareth-30 is a mixture of cetyl alcohol and stearyl alcohol, each ethoxylated with 30 units of ethylene oxide. The mixture of cetyl alcohol and stearyl alcohol is called cetearyl alcohol. Ceteareth-30 has the CAS number 68439-49-6 and can be purchased, for example, under the trade name Eumulgin B3 from BASF.

It has been found to be quite preferred if the composition contains both at least one nonionic surfactant of formula (T-I) and at least one nonionic surfactant of formula (T-II).

Other Optional Ingredients in the Agent

In addition to the ingredients (a1) and (a2) essential to the present disclosure already described, the composition may also contain further optional ingredients.

For example, the agent may contain a film-forming polymer. The film-forming polymer may be selected, for example, from the group including polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, explicitly very particularly preferred polyvinylpyrrolidone (PVP).

Further appropriate film-forming polymers can be selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization, or natural polymers have proven to be well suited.

Other particularly well-suited film-forming polymers can be selected from the homopolymers or copolymers of olefins, such as cycloolefins, butadiene, isoprene or styrene, vinyl ethers, vinyl amides, the esters or amides of (meth) acrylic acid having at least one $C_1$-$C_{20}$ alkyl group, an aryl group or a $C_2$-$C_{10}$ hydroxyalkyl group.

Other film-forming polymers may be selected from the homo- or copolymers of isooctyl (meth)acrylate; isononyl (meth)acrylate; 2-ethylhexyl (meth)acrylate; lauryl (meth) acrylate); isopentyl (meth)acrylate; n-butyl (meth)acrylate); isobutyl (meth)acrylate; ethyl (meth)acrylate; methyl (meth) acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth) acrylamides, in those with C2-C18 alkyl groups, such as N-ethyl-acrylamide, N-tert-butyl-acrylamide, le N-octylcrylamide; N-di(C1-C4)alkyl-(meth)acrylamide.

Other suitable anionic copolymers include copolymers of acrylic acid, methacrylic acid or their $C_1$-$C_6$ alkyl esters, as sold under the INCI declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Polymers on the market include Aculyn® 22 (Acrylate/ Steareth-20 Me-thacrylate Copolymer), Aculyn® 28 (Acrylate/Beheneth-25 Methacrylate Copolymer), Structure 2001® (Acryla-tes/Steareth-20 Itaconate Copolymer), Structure 3001® (Acrylate/Ceteth-20 Itaconate Copolymer), Structure Plus® (acrylate/aminoacrylate C10-30 alkyl PEG-20 itaconate copolymer), Carbopol® 1342, 1382, Ultrez 20, Ultrez 21 (acrylate/C10-30 alkyl acrylate crosspolymer), Synthalen W 2000® (acrylate/palmeth-25 acrylate copolymer) or Soltex OPT (acrylate/C12-22 alkyl methacrylate copolymer) distributed by Rohme and Haas.

The homo- and copolymers of N-vinylpyrrolidone, vinylcaprolactam, vinyl-(C1-C6)alkyl-pyrrole, vinyl-oxazole, vinyl-thiazole, vinylpyrimidine, vinylimidazole can be named as suitable polymers based on vinyl monomers.

Also suitable are the copolymers octylacrylamide/acrylates/butylaminoethyl methacrylate copolymer, such as those sold commercially under the trade names AMPHOMER® or LOVOCRYL® 47 from NATIONAL STARCH, or the copolymers of acrylates/octylacrylamides sold under the trade names DERMACRYL® LT and DERMACRYL® 79 from NATIONAL STARCH.

Suitable olefin-based polymers include homopolymers and copolymers of ethylene, propylene, butene, isoprene and butadiene.

In another version, block copolymers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

If, in principle, both anionic and cationic and/or nonionic polymers can be used in the composition as contemplated herein, it has proved particularly preferable not to use further ionic compounds or to use them only in small amounts. In other words, a particularly strong improvement in color intensity could be achieved when the agent was a predominantly non-ionic base and therefore contained cationic and anionic polymers either not at all or only in very small amounts. For this reason, it has been found to be particularly preferable if the total content of all anionic polymers contained in the agent is below 0.1% by weight. Furthermore, it has been found to be particularly preferred if the total content of all cationic polymers contained in the agent is below 0.1% by weight. The amount of catalytic or anionic polymer is related to the total weight of the agent.

In a further particularly preferred embodiment, a process as contemplated herein is exemplified in that—based on the total weight of the colorant (a)—the colorant is
the total content of all anionic polymers contained in the colorant (a) is below 0.1% by weight, and
the total content of all cationic polymers contained in the colorant (a) is below 0.1% by weight.

In addition to the non-ionic surfactants described above, the agents can in principle also contain one or more charged surfactants. The term surfactants refer to surface-active substances. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one –COO$^{(-)}$— or —SO$_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —$SO_3H$ group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino-propionates, aminoglycinate, imidazoliniumbetaines and sulfobetaines.

Examples of ampholytic surfactants are N-cocosalkylaminopropionate, cocosacylaminoethylaminopropionate and $C_{12}$-$C_{18}$-acyl sarcosine.

In addition, the products may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually including a hydrocarbon backbone (e.g., including one or two linear or branched alkyl chains) and the positive charge(s) being in the hydrophilic head group. Examples of cationic surfactants are quaternary ammonium compounds which, as hydrophobic radicals, may carry one or two alkyl chains with a chain length of 8 to 28 C atoms, quaternary phosphonium salts substituted with one or more alkyl chains with a chain length of 8 to 28 C atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of 0.1 to 45 wt. %, preferably 1 to 30 wt. % and most preferably 1 to 15 wt. %—based on the total weight of the respective agent.

Furthermore, the means as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

If, in principle, both anionic and cationic and/or non-ionic surfactants can be used in the composition as contemplated herein, it has proved particularly preferable not to use further ionic compounds or to use them only in small quantities. In other words, a particularly strong improvement in color intensity could be achieved when the agent was a predominantly non-ionic base and therefore contained cationic and anionic surfactants either not at all or only in very small amounts. For this reason, it has been found to be particularly preferable if the total content of all anionic surfactants contained in the formulation is below 0.1% by weight. Furthermore, it has been found to be particularly preferable if the total content of all cationic surfactants contained in the agent is below 0.1% by weight. The amount of catalytic or anionic surfactant is related to the total weight of the product.

In another very particularly preferred embodiment, a composition as contemplated herein is exemplified in that—based on the total weight of the colorant (a)—it comprises the total content of all anionic surfactants present in the colorant (a) is below 0.1% by weight, and the total content of all cationic surfactants contained in the colorant (a) is below 0.1% by weight.

The compositions may also contain other active ingredients, auxiliaries and additives, such as solvents, structurants such as glucose, maleic acid and lactic acid, hair-conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; polyphenols, in particular hydroxy cinnamic acids, 6,7-dihydroxycoumarins, hydroxybenzoic acids, catechins, tannins, leucoanthocyanidins, anthocyanidins, flavanones, flavones and flavonols; Ceramides or pseudoceramides; vitamins, provitamins and vitamin precursors; plant extracts; fats and waxes such as fatty alcohols, beeswax, montan wax and kerosenes; Swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, N20, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of 0.0001 to 25 wt. % each, 0.0005 to 15 wt. %, based on the total weight of the respective agent.

Average Water Content

The agent described above is a ready-to-use agent that can be applied to the keratinous material. This ready-to-use agent preferably has a high water content. It has been found that particularly suitable agents are those containing—based on the total weight of the agent—50.0 to 98.0% by weight, preferably 60.0 to 90.0% by weight, more preferably 70.0 to 90.0% by weight and most preferably 75.0 to 90.0% by weight of water.

In a further explicitly quite particularly preferred embodiment, an agent as contemplated herein is exemplified in that it contains—based on the total weight of the agent—50.0 to 98.0% by weight, preferably 60.0 to 90.0% by weight, further preferably 70.0 to 90.0% by weight and very particularly preferably 75.0 to 90.0% by weight of water.

pH Value of the Colorant (a)

The pH value of the colorant (a) is preferably adjusted to a neutral to alkaline pH value. Most preferably, the agent has an alkaline pH value in the range of 7.0 to 11.5 preferably from 8.0 to 11.0, and most preferably from 8.5 to 10.5. Under basic conditions, the amino-functionalized silicone polymer (a1) can be dissolved or dispersed particularly well and without protonation.

In the context of a further preferred embodiment, a process as contemplated herein is exemplified in that the colorant (a) contains water and has a pH of from 7.0 to 11.5 preferably from 8.0 to 11.0, and particularly preferably from 8.5 to 10.5.

To adjust the desired pH, the agent (a) and/or (b) may contain at least one alkalizing agent. The pH values for the purposes of the present disclosure are pH values measured at a temperature of 22° C.

As alkalizing agents, the agents may contain, for example, ammonia, alkanolamines and/or basic amino acids.

The alkanolamines which can be used in the composition of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore exemplified in that the agent as contemplated herein contains an alkanolamine selected from 2-aminoethan-1-ol and/or 2-amino-2-methylpropan-1-ol as alkalizing agent.

For the purposes of the present disclosure, an amino acid is an organic compound containing at least one protonatable amino group and at least one —COOH or —$SO_3H$ group in its structure. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than 7.0.

Basic α-amino carboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein is therefore exemplified in that the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In another very particularly preferred embodiment, a process as contemplated herein is exemplified in that the colorant (a) comprises at least one alkalizing agent selected from the group including ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Exposure of the Keratin Material to the Dyeing Agent (a).

In step (2) of the process as contemplated herein, the colorant (a) is allowed to act on the keratinous material for a period of 15 seconds to 10 minutes.

A major advantage of the dyeing process as contemplated herein is that an intensive color result can be achieved even in very short periods after short exposure times. For this reason, it is as contemplated herein to leave the colorant (a) on the keratin material only for comparatively short periods of time of 15 seconds to 10 minutes after its application.

Further shortening of the application time increases the convenience of use without sacrificing color intensity. For this reason, it is particularly preferred to leave the colorant (a) on the keratin material for even shorter periods of time, from 30 seconds to 5 minutes, especially preferably from 30 seconds to 2 minutes.

In a further preferred embodiment, a method as contemplated herein is. exemplified by:
(2) Exposure of the colorant (a) to the keratinous material for a period of 30 seconds to 5 minutes, preferably from 30 seconds to 2 minutes.

Rinsing Out the Dye (a)

Following the action of the colorant (a) on the keratin material, it is finally rinsed out under running water in step (3). A characteristic feature of the process as contemplated herein is that no further cosmetic agent different from the colorant (a) is used.

Running water is understood to be flowing tap water taken from the open tap of a drinking water pipe. In a normal water pipe, the water pressure is 3-5 bar.

In other words, in the process as contemplated herein, exactly one cosmetic agent, namely the coloring agent (a), is applied to the keratin material and rinsed out again under running water after the exposure time has ended. No other shampoo, conditioner or aftercare product is used.

In a further preferred embodiment, a method as contemplated herein is. exemplified by:

(3) Rinse out the dye (a) with water only.

In the course of the work leading to the present disclosure, it has been found that the rinsing process in step (3) must last at least 15 seconds. If the colorant (a) deposited in the form of a film on the keratin material meets the flowing water, the pH value of the previously preferably alkaline colorant (a) is lowered to the neutral range. In this context, it has been found that the neutral pH value is the prerequisite for immobilizing the film built up from the colorant (a) on the keratin material for as long as possible. If the rinsing process lasts at least 15 seconds, the pH value can be lowered sufficiently. However, even better durability of the dye is obtained if the keratin material is rinsed for longer than 15 seconds in step (3). For this reason, it has been found to be particularly preferred to rinse the colorant (a) in step (3) of the process for a period of 30 seconds to 3 minutes and explicitly very particularly preferred from 45 seconds to 2 minutes.

In a further preferred embodiment, a method as contemplated herein is. exemplified by:

(3) Rinsing the colorant (a) under running water for a period of from 30 seconds to 5 minutes, preferably from 30 seconds to 3 minutes and most preferably from 45 seconds to 2 minutes.

Following rinsing, the keratin material can be dried, for example at room temperature or in a stream of air at 25 to 45° C.

Sequence of the Process Steps

The method as contemplated herein comprises steps (1) to (3).

In step (1), the colorant (a) is applied or applied. The action of the coloring agent on the keratin material in step (2) can only take place after its application. The rinsing of the coloring agent (a) in step (3) takes place after their action in step (2).

Examples

1. Formulations

The following formulations were prepared (all data in % by weight, unless otherwise stated)

|  | Dyeing agent (a) |
|---|---|
| Cetyl alcohol | 3.6 g |
| Stearyl alcohol | 2.0 g |
| Paraffinum Liquidum | 2.0 g |
| Ceteareth-30 (Cetearyl alcohol, ethoxylated 30 EO) | 1.2 g |
| Brij S 100 PA SG (stearyl alcohol, ethoylated 100 EO, Croda) | 0.6 g |
| Cutina GMS V (INCI: Glyceryl stearate, glyceol mono/dipalmitate/stearate) CAS No. 85251-77-0 | 0.6 g |
| 1.2-propanediol | 6.2 g |
| Lavanya Zuni (organic pigment, Neelikon Red, 111P0200, CI 12490) | 1.5 g |
| Dow Corning 2-8566 (Siloxanes and Silicones, 3-[(2-Aminoethyl)amino]-2-methylpropyl Me, Di-Me-Siloxane" | 2.5 g |
| Ammonia (25% aqueous solution) | ad pH 9.5 |
| Water | Ad 100 |

Post-Treatment Agent (NBM)

|  | (NBM) |
|---|---|
| Citric acid | ad pH 3.0 |
| Water | ad 100 |

2. Application

The dye (a) was applied to hair strands (Kerling, Euro-natural hair white, liquor ratio: 1 g of colorant (a) per g of hair strand). The agent was left to act for three minutes.

If the post-treatment agent was applied, 4 g of post-treatment agent (NBM) per g of hair strand was applied to the strands still exposed to agent (a).

|  | Comparison (V1) | Invention (E1) |
|---|---|---|
| Dyeing agent (a) | apply and leave on for 3 min | apply and leave on for 3 min |
| Post-treatment agent (NBM) | apply and leave on for 1 min | ---- |
| Running water | wash out for 60 seconds | wash out for 60 seconds |
| Color Intensity | red +++ | red +++ |

Color intensity: − = uncolored + = low ++ = average +++ = very good

When the process as contemplated herein (E1) was carried out, it was possible to achieve a color intensity comparable to the process (V1). However, the method (E1) as contemplated herein comprises fewer steps and is therefore shorter and more convenient for the user than the method (V1).

Accordingly, the process (E1) was able to increase user comfort while maintaining color intensity.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for dyeing keratinous material comprising the following steps:
   (1) applying a coloring agent (a) to the keratinous material, wherein the coloring agent (a) comprises:
      (a1) at least one amino-functionalized silicone polymer, and
      (a2) at least one colorant compound,
   (2) allowing the coloring agent (a) to act on the keratinous material for a period of 15 seconds to 10 minutes, and
   (3) rinsing out the dye (a) under running water for a period of 15 seconds to 10 minutes, wherein no further cosmetic agent other than the coloring agent (a) is used in the process.

2. The process according to claim 1, wherein the coloring agent (a) comprises at least one amino-functionalized silicone polymer (a1) having at least one secondary amino group.

3. The process according to claim 1, wherein the coloring agent (a) comprises at least one amino-functionalized silicone polymer (a1) comprising at least one structural unit of the formula (Si amino),

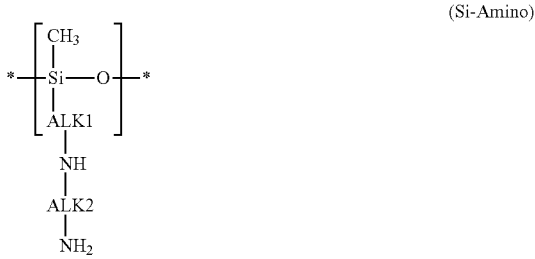

(Si-Amino)

where
ALK1 and ALK2 independently represent a linear or branched $C_1$-$C_{20}$ divalent alkylene group.

4. The process according to claim 1, wherein the coloring agent (a) comprises at least one amino-functionalized silicone polymer (a1) which comprises structural units of the formula (Si-I) and of the formula (Si-II)

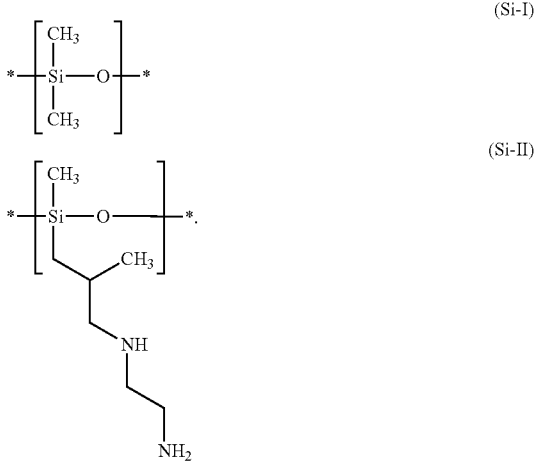

5. The process according to claim 1, wherein the coloring agent (a) comprises—based on the total weight of the colorant (a)—one or more amino-functionalized silicone polymers (a1) in a total amount of from 0.1 to 8.0% by weight.

6. The process according to claim 1, wherein the coloring agent (a) comprises at least one colorant compound (a2) selected from the group of pigments, direct dyes, photochromic dyes and thermochromic dyes.

7. The process according to claim 1, wherein the coloring agent (a) comprises at least one colorant compound (a2) selected from the group consisting of colored metal oxides, metal hydroxides, metal oxide hydrates, silicates, metal sulfides, complex metal cyanides, metal sulfates, bronze pigments, colored mica pigments coated with at least one metal oxide, colored mica pigments coated with at least one metal oxychloride, colored mica-based pigments coated with at least one metal oxide, and colored mica-based pigments coated with at least one metal oxychloride.

8. The process according to claim 1, wherein the coloring agent (a) comprises at least one colorant compound (a2) selected from the group consisting of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, and red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

9. The process according to claim 1, wherein the coloring agent (a) comprises—based on the total weight of the coloring agent (a)—one or more pigments (a2) in a total amount of from 0.01 to 10.0% by weight.

10. The process according to claim 1, wherein the coloring agent (a) comprises at least one solvent (a3) selected from the group consisting of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol.

11. The process according to claim 1, wherein the coloring agent (a) comprises—based on the total weight of the coloring agent (a)—0.25 to 20.0% by weight of 1,2-propylene glycol.

12. The process according to claim 1, wherein the coloring agent (a) comprises one or more fatty constituents selected from the group consisting of the $C_{12}$-$C_{30}$ fatty alcohols, the $C_{12}$-$C_{30}$ fatty acid triglycerides, the $C_{12}$-$C_{30}$ fatty acid monoglycerides, the $C_{12}$-$C_{30}$ fatty acid diglycerides and/or hydrocarbons.

13. The process according to claim 1, wherein the coloring agent (a) comprises one or more $C_{12}$-$C_{30}$ fatty alcohols selected from the group of dodecan-1-ol, tetradecan-1-ol, hexadecan-1-ol, octadecan-1-ol, eicosan-1-ol, heneicosan-1-ol, docosan-1-ol, (9Z)-octadec-9-en-1-ol, (9E)-Octadec-9-en-1-ol, (9Z,12Z)-Octadeca-9,12-dien-1-ol, (9Z,12Z,15Z)-Octadeca-9,12,15-trien-1-ol, (9Z)-Eicos-9-en-1-ol, (5Z,8Z,11Z,14Z)-Eicosa-5, 8,11,14-tetraen-1-ol, (13Z)-docos-13-en-1-ol), (13E)-docosen-1-ol), 2-octyl-dodecanol, 2-hexyl-dodecanol and/or 2-butyl-dodecanol.

14. The process according to claim 1 , wherein the coloring agent (a) comprises at least one nonionic surfactant of the formula (T-I),

(T-I)

wherein
Ra represents a saturated or unsaturated, unbranched or branched $C_8$-$C_{24}$ alkyl group, and
n is an integer from 10 to 40.

15. The process according to claim 1, wherein—based on the total weight of the coloring agent (a)—
the total content of all anionic surfactants present in the coloring agent (a) is less than 0.1% by weight, and
the total content of all cationic surfactants included in the coloring agent (a) is less than 0.1% by weight.

16. The process according to claim 1, wherein—based on the total weight of the coloring agent (a)— the total content of all anionic polymers included in the coloring agent (a) is less than 0.1% by weight, and the total content of all cationic polymers included in the coloring agent (a) is less than 0.1% by weight.

17. The process according to claim 1, wherein the coloring agent (a) comprises water and has a pH of from 7.0 to 11.5.

18. The method process according to claim 1, wherein allowing the coloring agent (a) to act on the keratinous material comprises exposing the coloring agent (a) to the keratinous material for a period of 30 seconds to 5 minutes.

19. The process according to claim 1, comprising rinsing the coloring agent (a) under running water for a period of from 30 seconds to 5 minutes.

* * * * *

UNITED STATES PATENT AND TRADEMARK OFFICE
CERTIFICATE OF CORRECTION

| | | |
|---|---|---|
| PATENT NO. | : 11,786,452 B2 | Page 1 of 1 |
| APPLICATION NO. | : 17/620091 | |
| DATED | : October 17, 2023 | |
| INVENTOR(S) | : Constanze Kruck, Sandra Hilbig and Daniela Kessler-Becker | |

It is certified that error appears in the above-identified patent and that said Letters Patent is hereby corrected as shown below:

In the Specification

Column 6, Line 59 change "$C_1$ - 4" to --C1-4--.
Column 8, Line 46 change "$(CH\ 2)_{zz}$" to --$(CH_2)_{zz}$--.
Column 8, Line 51 change "X of X2" to --X of $X_2$--.
Column 9, Line 33 change "$CH_2CH_2CH_2H3$" to --$CH_2CH_2CH_2H_3$--.
Column 15, Line 9 change "nitro-azo" to --nitro azo--.
Column 18, Line 1 change "(CI C.I. 18065)" to --(CI 18065)--.
Column 22, Line 26 change "C=C" to --C-C--.
Column 27, Line 18 change "$R^7C_o$" to --$R^7CO$--.
Column 28, Line 51 change "$C_{16}$- to Cis" to --$C_{16}$- to $C_{18}$--.
Column 32, Line 29 change "hydroxy cinnamic acids" to --hydroxycinnamic acids--.
Column 32, Line 43 change "N20" to --$N_2O$--.

In the Claims

Column 39, Line 8, Claim 18 change "method process" to --process--.

Signed and Sealed this
Twenty-fourth Day of December, 2024

Derrick Brent
*Acting Director of the United States Patent and Trademark Office*